US00PP36607P2

(12) United States Plant Patent
Bean et al.

(10) Patent No.: US PP36,607 P2
(45) Date of Patent: Apr. 15, 2025

(54) ***AGAPANTHUS* PLANT NAMED 'DWAgHyb18'**

(50) Latin Name: ***Agapanthus* hybrid**
Varietal Denomination: DWAgHyb18

(71) Applicant: De Wet Plant Breeders, Johannesburg (ZA)

(72) Inventors: Quinton Bean, Northriding (ZA); Charles Andrew De Wet, Sandton (ZA)

(73) Assignee: DE WET PLANT BREEDERS, Sandton (ZA)

( * ) Notice: Subject to any disclaimer, the term of this patent is extended or adjusted under 35 U.S.C. 154(b) by 0 days.

(21) Appl. No.: 18/910,392

(22) Filed: Oct. 9, 2024

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
See application file for complete search history.

*Primary Examiner* — Susan McCormick Ewoldt
(74) *Attorney, Agent, or Firm* — Penny J. Aguirre

(57) ABSTRACT

A new cultivar of *Agapanthus* plant named 'DWAgHyb18' that is characterized by its good resistance to root and crown rot, its umbels of flowers that are white and green in color opening from green flower buds, its long flowering period with modest re-blooming, its medium plant height, and its semi-evergreen growth habit.

2 Drawing Sheets

Botanical classification: *Agapanthus* hybrid.
Varietal denomination: 'DWAgHyb18'.

CROSS-REFERENCE TO A RELATED APPLICATION

This application is co-pending with a U.S. Plant Patent Application filed for a plant derived from the same breeding program that is entitled *Agapanthus* Plant Named 'DWAgHybPi' (U.S. Plant Patent Application pending)*.
*(Applicant gives the examiner the authority to replace the U.S. Plant Patent Application No. with a Patent No. if applicable and delete this statement.)

BACKGROUND OF THE INVENTION

The present invention relates to a new and distinct cultivar of *Agapanthus* of hybrid origin and will be referred to hereafter by its cultivar name, 'DWAgHyb18'. 'DWAgHyb18' represents a new perennial grown for landscape and container use.

The new cultivar was derived from a controlled breeding program by the Inventors in Hartebeespoort, North West Province, South Africa. The goal of the breeding program was to develop a new a cultivar of *Agapanthus* with a long blooming period that re-blooms and is resistant to rot caused by *Erwinia* sp. The Inventors made a cross in November of 2018 between unnamed and unpatented proprietary plants of *Agapanthus* from the Inventors' breeding program as both the female and male parents. The Inventors selected 'DWAgHyb18' in November of 2021 as a single unique plant amongst the seedlings that resulted from the above cross.

Asexual propagation of the new cultivar was first accomplished by division by one of the Inventors in Hartebeespoort, North West Province, South Africa in November of 2021. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'DWAgHyb18' as a distinct cultivar of *Agapanthus*.

1. 'DWAgHyb18' exhibits good resistance to root and crown rot.
2. 'DWAgHyb18' exhibits umbels of flowers that are white and green in color opening from green flower buds.
3. 'DWAgHyb18' exhibits a long flowering period with modest re-blooming.
4. 'DWAgHyb18' exhibits a medium plant height.
5. 'DWAgHyb18' exhibits a semi-evergreen growth habit.

The female parent of 'DWAgHyb18' differs from 'DWAgHyb18' in having more tubular shaped flowers that open less and in having more deciduous traits. The male parent of 'DWAgHyb18' differs from 'DWAgHyb18' in having flowers that have less green coloration in the flowers and in having more deciduous traits. 'DWAgHyb18' can be most closely compared to the *Agapanthus* cultivars 'WP001' (U.S. Plant Pat. No. 27,357), 'Snow Ripple' (not patented) and 'DWAgHybPi'. 'WP001' and 'Snow Ripple' are similar to 'DWAgHyb18' in having white flowers. 'WP001' and 'Snow Ripple' both differ from 'DWAgHyb18' in having flowers with no green coloration and in being evergreen varieties. 'DWAgHybPi' is similar to 'DWAgHyb18' in having disease resistance, in having a reblooming habit, and a semi-evergreen growth habit. 'DWAgHybPi' differs from 'DWAgHyb18' in having pink and white flowers.

STATEMENT REGARDING PRIOR DISCLOSURES BY THE INVENTORS

The Applicant asserts that no publications or advertisements relating to sales, offers for sale, or public distribution occurred more than one year prior to the effective filing date of this application. Any information about the claimed plant would have been obtained from a direct or indirect disclosure from the Inventors. The Applicant claims a prior art exemption under 35 U.S.C. 102(b)(1) for disclosures and/or sales that fall within a one-year grace period to the filing date. Disclosures include website listings by Dobies, Van Meuwen, Fairweather's Plant Shop, Thompson & Morgan, Waitrose Garden, B & Q, Woodlands Garden Centre, Suttons Seeds, and The Big Plant Nursery.

BRIEF DESCRIPTION OF THE DRAWINGS

The accompanying color photographs illustrate the overall appearance and distinct characteristics of the new *Agapanthus*.

The photograph in FIG. 1 was taken of a plant 2 years in age as grown outdoors in a 19-cm container in Hazerwoude-Dorp, The Netherlands and provides a side view of a plant of 'DWAgHyb18' in bloom.

Figure 1:
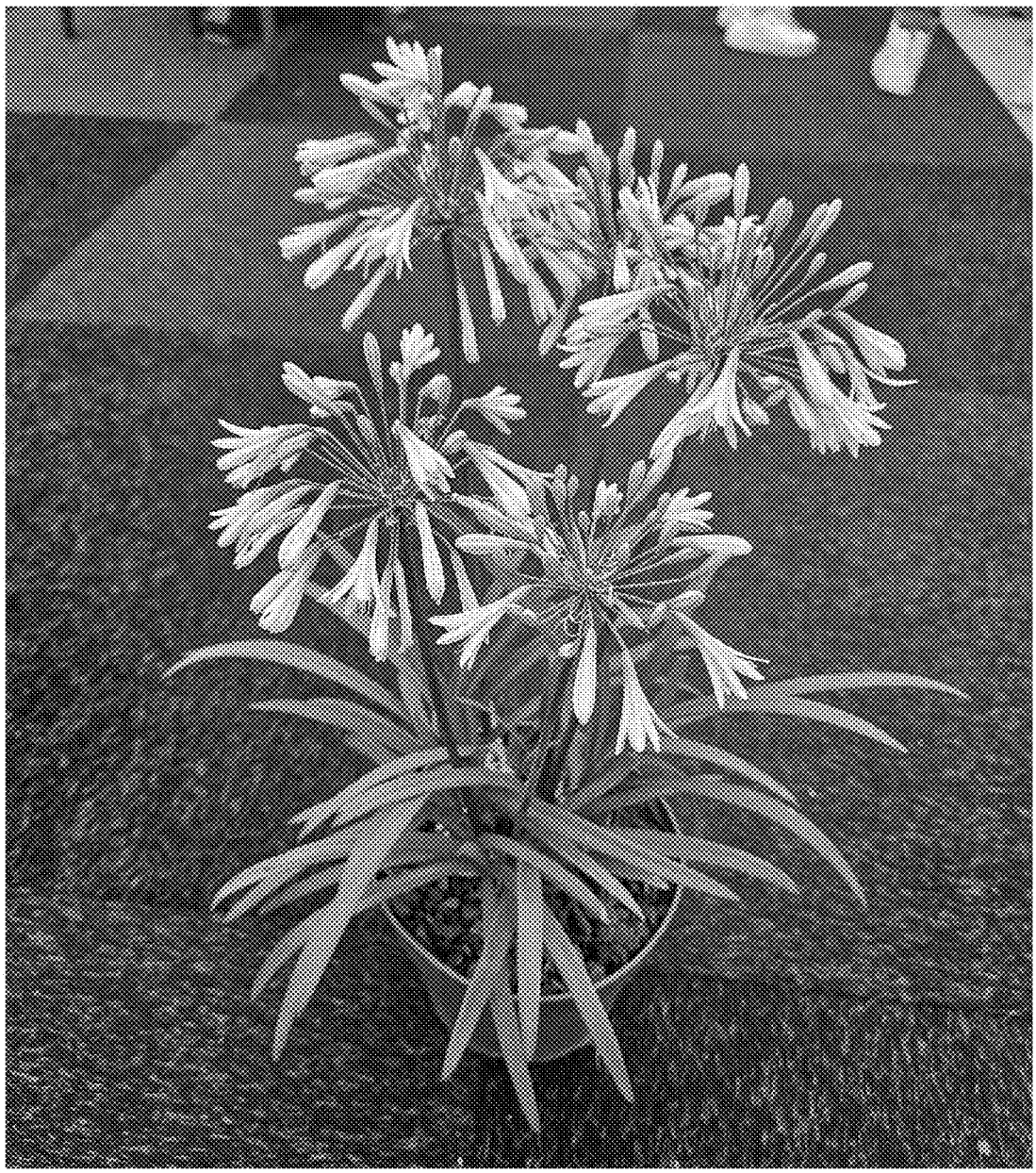
Figure 2:
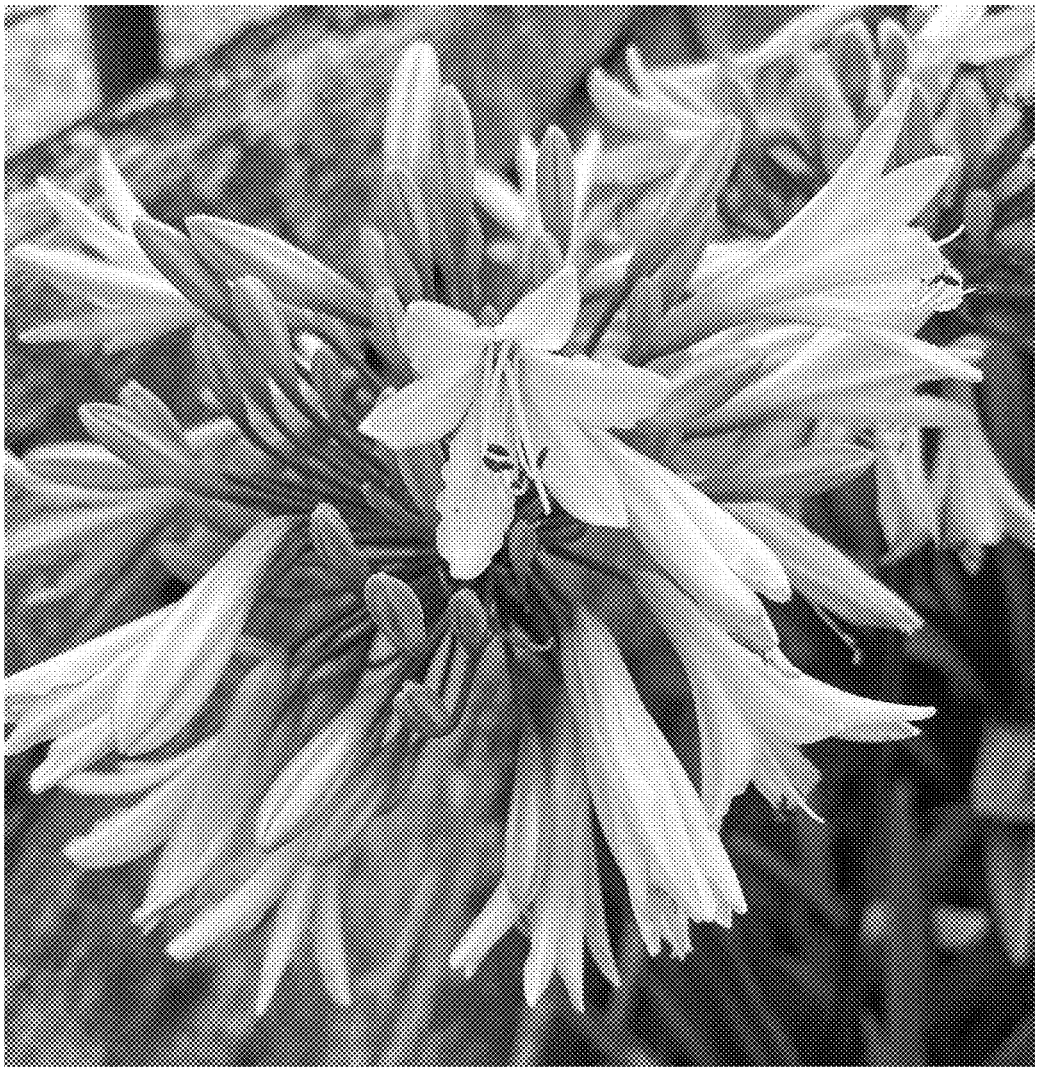

The photograph in FIG. 2 was taken of a plant 2 years in age as grown outdoors in a 19-cm container in Beaulieu, The United Kingdom and provides a close-up view of an inflorescence of 'DWAgHyb18'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 3-year-old plants of 'DWAgHyb18' as grown outdoors in 19-cm containers in Hartebeespoort, North West Province, South Africa. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Blooming period*.—Main bloom early to mid-summer in South Africa, sporadically re-blooming the rest of the growing season.

*Plant type*.—Herbaceous perennial, semi-evergreen.

*Plant habit*.—Compact, basal rosettes with inflorescences emerging from the rosette center.

*Height and spread*.—65 cm in height, 71 cm in width as a 3-year-old plant grown in a container.

*Cold hardiness*.—At least to U.S.D.A. Zone 8.

*Diseases and pests*.—Good resistance has been observed to crown rot caused by *Fusarium* sp. and root rot caused by *Erwinia* sp., no resistance or susceptibility to pests has been observed.

*Root description*.—Thick and fleshy, 161C in color.

*Propagation*.—Tissue culture (preferred) and division.

*Growth rate*.—Vigorous.

*Number of shoots* (*rosettes*).—An average of 1.

Foliage description:

*Leaf shape*.—Ligulate.

*Leaf division*.—Simple.

*Leaf base*.—Truncate.

*Leaf arrangement*.—2-ranked, arranged in shoots an average of 3.5 cm diameter at base.

*Leaf apex*.—Narrow acute.

*Leaf aspect*.—Emerging leaves erect, then cascade.

*Leaf venation*.—Parallel, both surfaces 144C in color.

*Leaf margins*.—Entire.

*Leaf size*.—Up to 43 cm in length and up to 2.1 cm in width.

*Leaf surface*.—Smooth, glabrous, and dull on upper and lower surface.

*Leaf number*.—Average of 120 leaves per rosette.

*Foliage density*.—Sparse to medium.

*Leaf color*.—Young and mature lower surface 137A, base 144C to 144D (no anthocyanin present), young and mature upper surface 137B to 137C, base 144C to 144D, with 145C.

*Leaf attachment*.—Sessile to base.

Flower description:

*Inflorescence type*.—Dense umbel.

*Flower fragrance*.—None.

*Flower type*.—Rotate, campanulate, base of tepals fused.

*Flower number*.—An average of 17 open flowers and 38 buds.

*Inflorescence size*.—Average of 8 cm in height and 11 cm in diameter.

*Flower size*.—An average of 3.8 cm in depth and 3 cm in diameter.

*Lastingness of inflorescence*.—Average 7 days.

*Flower aspect*.—Upward to downward.

*Peduncle*.—Very strong, oval in shape, held primarily upright, average of 50 cm in length and 7 mm in width, glabrous and slightly glaucous surface, satiny, color; 137B to 137C, no anthocyanin present.

*Pedicels*.—Very strong, oval in shape, aspect held erect to outward, average of 2.3 cm in length and 1 mm in width, glabrous surface, color; 144A.

*Flower buds*.—Obelliptic in shape, average of 1.8 cm in length and 5 mm in width, 144C to 144D in color with base 144B.

*Tepals* (*perianth*).—6, oblanceolate in shape, lower 25% fused, entire to slightly undulate margins, apex is rounded to acute, glabrous and satiny on inner and outer surfaces, thick substance, an average of 3.3 cm in length and 6 mm in width, color; upper surface NN155A, striped 144C, lower surface NN155A, striped 144C and 144B.

*Bracts*.—1 per inflorescence, ovate to lanceolate in shape, acuminate apex, truncate base, glabrous and matte surface, up to 4 cm in length and 1.7 cm in width, color; 144A to 144C.

Reproductive organs:

*Gynoecium*.—1 pistil, average of 2.3 cm in length, stigma is narrow clavate in shape and NN155A in color, style is 2.3 cm in length, 1 mm in diameter, color; NN155A, ovary is oblong in shape, 6 mm in length, 3 mm in width and 144B in color, pistillodes not present.

*Androecium*.—6 stamens, anthers are dorsifixed and obcordate in shape, extrusion absent to weak, average of 2 cm in length, and 202A in color, filament is 2.4 cm in length, N155Ain color, pollen is low, not able to measure pollen color as they are not clearly visible, staminodes not present.

*Fruit/seed*.—Have not been observed to date.

It is claimed:

1. A new and distinct cultivar of *Agapanthus* plant named 'DWAgHyb18' as herein illustrated and described.

* * * * *